(12) United States Patent
Kobayashi

(10) Patent No.: US 7,198,746 B1
(45) Date of Patent: Apr. 3, 2007

(54) METHOD OF CONNECTION WITH SYNTHETIC RESIN MEMBER

(75) Inventor: Kaoru Kobayashi, Tokyo (JP)

(73) Assignee: Kabushiki Kaisha Top, Tokyo (JP)

( * ) Notice: Subject to any disclaimer, the term of this patent is extended or adjusted under 35 U.S.C. 154(b) by 0 days.

(21) Appl. No.: 10/110,401

(22) PCT Filed: Mar. 31, 2000

(86) PCT No.: PCT/JP00/02106

§ 371 (c)(1),
(2), (4) Date: Apr. 12, 2002

(87) PCT Pub. No.: WO01/26884

PCT Pub. Date: Apr. 19, 2001

(30) Foreign Application Priority Data

Oct. 14, 1999 (JP) ................................. 11-291783

(51) Int. Cl.
*B29C 65/00* (2006.01)
*B29C 53/08* (2006.01)
*A61M 5/14* (2006.01)
*B29C 43/22* (2006.01)

(52) U.S. Cl. ........................ 264/249; 264/339; 264/503; 604/240

(58) Field of Classification Search .............. 264/500, 264/503, 239, 249, 266, 267, 285, 293, 295, 264/296, 339; 277/65, 316, 602, 924; 285/238, 285/256, 260, 286.2, 282, 282.7, 382, 285.1, 285/286.1, 382.7; 222/570; 403/2, 27, 316, 403/602, 924; 29/443, 437, 439, 440, 243.5, 29/508–511, 243.57, 513; 604/240, 905
See application file for complete search history.

(56) References Cited

U.S. PATENT DOCUMENTS

| 1,241,654 | A |   | 10/1917 | Osgood |         |
|-----------|---|---|---------|--------|---------|
| 3,469,579 | A |   | 9/1969  | Hubert |         |
| 3,578,519 | A |   | 5/1971  | Baumann |        |
| 4,219,912 | A |   | 9/1980  | Adams  |         |
| 4,773,553 | A | * | 9/1988  | Van Brocklin | 215/272 |
| 4,932,114 | A |   | 6/1990  | Morse et al. |    |
| 6,382,442 | B1 | * | 5/2002 | Thibault et al. | 215/249 |

FOREIGN PATENT DOCUMENTS

| BE | 828559  | A | 8/1975 |
| FR | 2066752 | A | 8/1971 |

(Continued)

*Primary Examiner*—Chris Fiorilla
*Assistant Examiner*—Sing Po Chan
(74) *Attorney, Agent, or Firm*—Birch, Stewart, Kolasch & Birch, LLP

(57) ABSTRACT

A method for connecting a member includes the steps of providing a member to be connected having a flange at an end to be connected with a bucklingly deformable synthetic resin member having an overhanging portion which overhangs the flange. A synthetic resin member is selected from the group a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane. The overhanging portion of the synthetic resin member is disposed over the flange of the member to be connected with the tip of the overhanging portion being bucklingly deformed toward the member to be connected to the extent that stress rupture does not occur. The flange is locked by the bucklingly deformed tip of the overhanging portion.

8 Claims, 4 Drawing Sheets

FOREIGN PATENT DOCUMENTS

| | | |
|---|---|---|
| JP | 136740/1982 | 8/1982 |
| JP | 58-163641 A | 9/1983 |
| JP | 61-079622 A | 4/1986 |
| JP | 61-083021 A | 4/1986 |
| JP | 01-204676 A | 8/1989 |
| JP | 11-058521 A | 3/1999 |

* cited by examiner

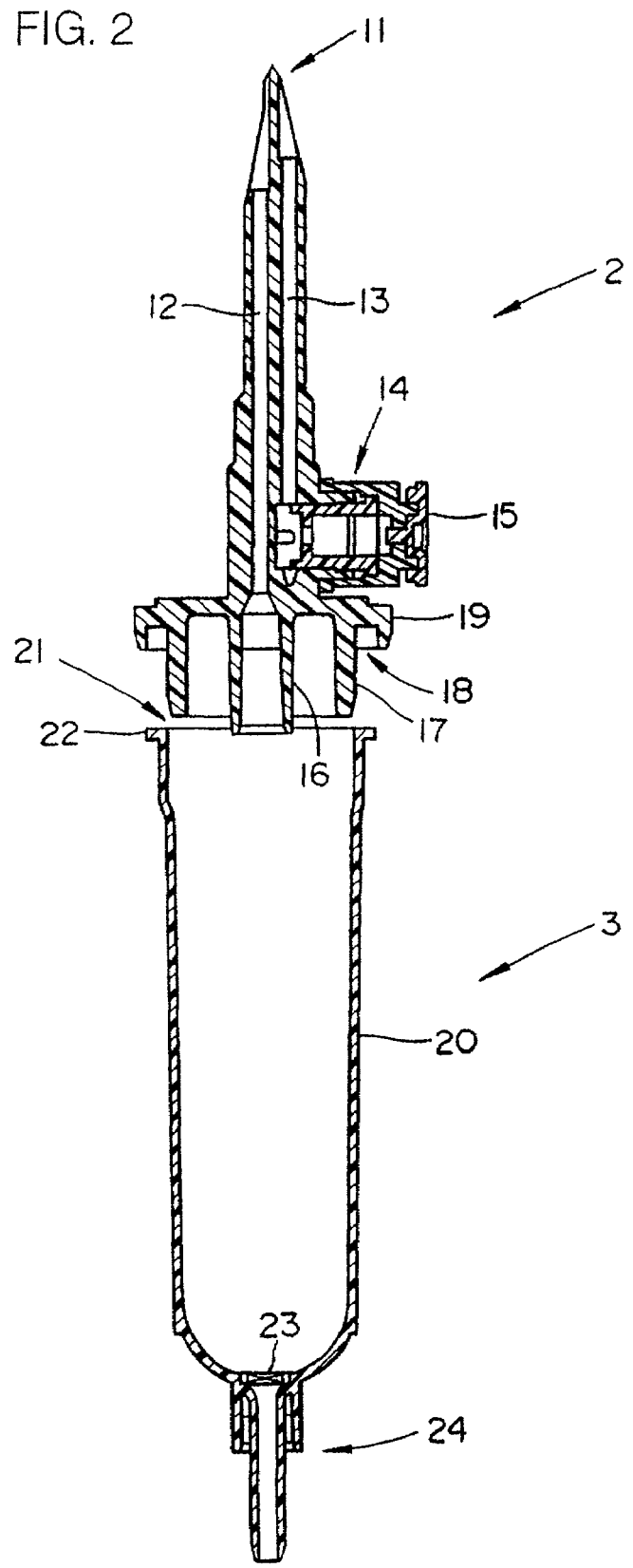

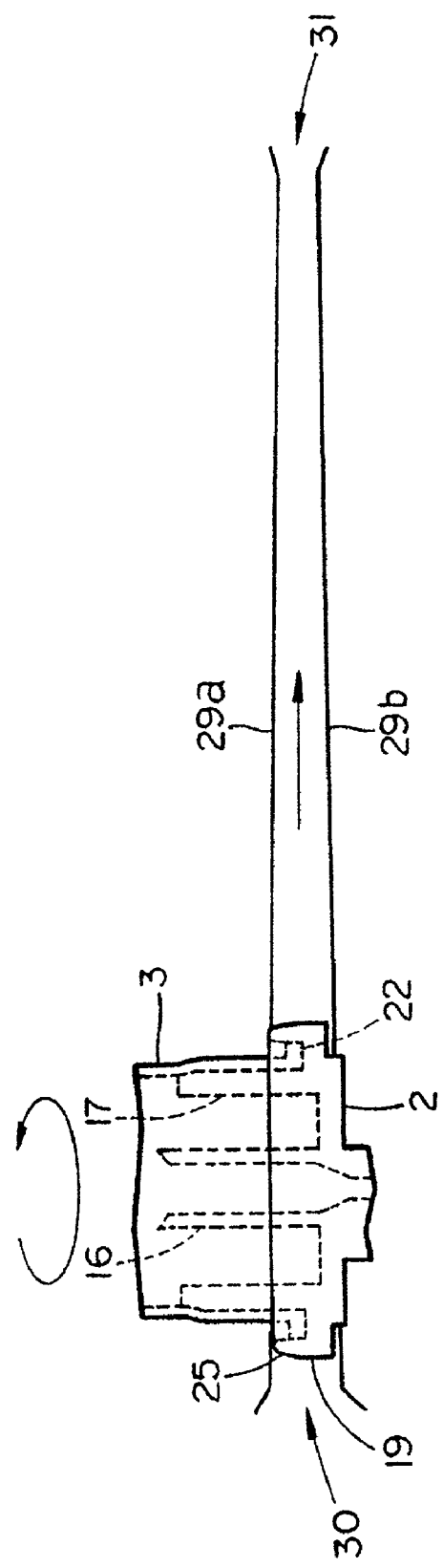

METHOD OF CONNECTION WITH SYNTHETIC RESIN MEMBER

TECHNICAL FIELD

The present invention relates to a method of connecting a synthetic resin member with other members made of a synthetic resin, metal, glass, ceramic and the like.

BACKGROUND ART

A synthetic resin member is generally connected to other members by means of adhesion. However, use of an adhesive is not desirable in some case or the synthetic resin member may have to be connected to a member which is not suitable for adhesion.

For example, a transfusion set 1 used as a medical instrument, as shown in FIG. 1, comprises a spike needle 2 which pierces a liquid container such as a transfusion bag which is not shown and a drip chamber 3 which is connected to the lower end of the spike needle 2 and has a substantially cylindrical shape.

Since the spike needle 2 is required to have enough hardness to pierce a sealing rubber cap attached to the above transfusion bag, it is generally formed of an acrylonitrile-butadiene-styrene copolymer resin (ABS resin). Meanwhile, the drip chamber 3 is transparent so as to observe a dripping state of a drug and is required to be formed of a soft resin so as to make fine adjustments to a dripping amount of liquid and pump and introduce a drug by being squeezed and released repeatedly at the start of transfusion.

The drip chamber 3 is conventionally formed of a soft vinyl chloride resin, for example.

Although the above vinyl chloride resin has good adhesion to the above ABS resin, it is desirable not to rely on adhesion as much as possible in order to avoid introduction of an adhesive itself or solvents contained in an adhesive into a living body at the time of transfusion.

Further, in recent years, the above drip chamber 3 is formed of such a resin as a polypropylene or an olefinic elastomer rather than a vinyl chloride resin. Use of a resin such as a polypropylene or an olefinic elastomer makes it possible to decrease the thickness of the drip chamber 3 as compared with the vinyl chloride resin. Therefore, the above resin is advantageous from the viewpoint of production costs because an amount of a resin used is decreased and a molding cycle is shortened.

However, since the above resin such as a polypropylene or an olefinic elastomer has extremely low adhesion to the ABS resin, it requires pretreatment for modifying its surface such as primer treatment, flame treatment, ozone treatment, plasma treatment or corona discharge treatment to be adhered to the ABS resin, thereby making the operation of such a resin complicated disadvantageously.

Further, in place of adhesion, it is considered that the drip chamber 3 formed of the resin such as a polypropylene or an olefinic elastomer is press-fitted into a space formed in the spike needle 2 formed of the above ABS resin by means of mutual elastic forces.

In this case, an undercut is provided in the portion of the spike needle 2 to which the drip chamber 3 is press-fitted so as to reinforce the fit. However, the dimensional accuracy of the undercut must be high to improve fittability, thereby making it difficult to produce the undercut. Further, when the press-fitted drip chamber 3 is pumped as described above, the drip chamber 3 may fall off or a drug or the like may leak.

Further, it is also considered that the spike needle 2 formed of the same resin such as a polypropylene or an olefinic elastomer as that constituting the drip chamber 3 and the drip chamber 3 are fused with each other by means of ultrasound. However, fusion of an olefinic resin by means of ultrasound has the disadvantage that conditions therefor are extremely limited. Further, when the material of the spike needle 2 is a resin such as a polypropylene or an olefinic elastomer, incorporation of a filler into the above resin must be considered in order to secure the hardness of the spike needle 2 which is sufficient for the spike needle 2 to pierce a sealing rubber cap attached to the above transfusion bag.

Under the above circumstances, development of a technology which can connect the spike needle 2 formed of an ABS resin and the drip chamber 3 formed of such a resin as soft vinyl chloride, a polypropylene or an olefinic elastomer to each other regardless of the degree of adhesion between the above resins has been desired.

DISCLOSURE OF THE INVENTION

The present invention has been invented under the above circumstances. It is an object of the present invention to provide a method of connecting a synthetic resin member with other members made of a synthetic resin, metal, glass, ceramic and the like.

As a method of connecting a synthetic resin member with other members, a method in which the synthetic resin member is subjected to plastic deformation and caused to engage other members is conceivable.

For example, the above synthetic resin member such as an injection-molded thermoplastic resin has the characteristic that after a molten resin is injection molded and cured in a given shape in a mold, it tries to keep the shape.

Therefore, even if the above synthetic resin member is deformed by application of stress, it restores its original shape either immediately or with time after the stress is removed.

Further, even if it remains deformed to some extent, it may restore its original shape when heated after deformation.

Further, the above synthetic resin member generally becomes cracked and is lead to stress rupture when an attempt is made to deform irreversibly.

However, according to studies made by the present inventor, it has been found that some of synthetic resins which may constitute the above synthetic resin member are first bucklingly deformed, then cracked and lead to stress rupture when stress is applied.

The buckling deformation of the synthetic resins is plastic deformation.

Therefore, the synthetic resins do not restore original shapes even if heat is applied. Further, since the bucklingly deformed portions are not lead to stress rupture, they have sufficient strength to engage other members.

Accordingly, to achieve the above object, the connection method of the present invention is a method of connecting a cylindrical body having a flange at its end with a synthetic resin member having a lagging tube to be fitted onto the flange and made of only a bucklingly deformable synthetic resin, wherein the lagging tube of the synthetic resin member is fitted onto the flange of the cylindrical body, the tip of the lagging tube is bucklingly deformed toward the cylindrical body by exerting only an external force on the tip of the lagging tube to the extent that stress rupture does not occur, and the flange is locked by the bucklingly deformed tip of the lagging tube.

The connection method of the present invention can be used to connect a cylindrical body with a synthetic resin member to be fitted onto the cylindrical body.

The cylindrical body has a flange at an end at which it is connected to the synthetic resin member.

The synthetic resin member has a lagging tube to be fitted onto the flange which is made of a bucklingly deformable synthetic resin member.

The synthetic resin member itself may be a cylindrical body and may be a lid of the cylindrical body having the flange.

In the connection method of the present invention, firstly, the lagging tube of the synthetic resin member is fitted onto the flange of the cylindrical body.

Then, stress is applied to the tip of the lagging tube to plastic-deform the tip of the lagging tube toward the cylindrical body.

At this point, the plastic deformation is carried out such that the tip of the lagging tube is bucklingly deformed to the extent that stress rupture does not occur.

As a result, the bucklingly deformed tip of the lagging tube engages the flange of the cylindrical body.

The tip of the lagging tube, as described above, does not restore its original shape even if heat is applied since it is bucklingly deformed.

Further, since it does not undergo stress rupture, it has sufficient strength to engage other members. Therefore, the synthetic resin member can lock the flange of the cylindrical body by the tip of the lagging tube so as to prevent the cylindrical body from falling off.

In the connection method of the present invention, the synthetic resin member preferably has a contact portion to be in contact with the flange of the cylindrical body at the base of the lagging tube. The synthetic resin member has the contact portion so that the tip of the lagging tube can be bucklingly deformed toward the cylindrical body with the flange in contact with the contact portion and the flange can be held and locked between the bucklingly deformed tip of the lagging tube and the contact portion.

In the connection method of the present invention, the above buckling deformation is carried out by pressing a rotatably pivoted roller, while rotating, against the tip of the lagging tube continuously with a predetermined pressing force for a given time period. When the buckling deformation is performed as described above, stress can be applied to the tip of the lagging tube uniformly, and the tip of the lagging tube can be bucklingly deformed to the extent that stress rupture does not occur. Further, rotation of the roller prevents formation of friction scars on the tip of the lagging tube, whereby appearance of good quality can be obtained.

In the connection method of the present invention, the synthetic resin member is made of a synthetic resin whose bucklingly deformed portion becomes whitened. In the present invention, the tip of the lagging tube of the synthetic resin member is bucklingly deformed toward the cylindrical body to whiten the bucklingly deformed portion, and the flange of the cylindrical body is locked by the bucklingly deformed tip of the lagging tube. Thereby, buckling deformation of the synthetic resin member can be determined from the outside according to the presence or absence of the whitened potion, and the quality of a product can be evaluated with ease.

As the synthetic resin whose bucklingly deformed portion becomes whitened, one resin selected from the group consisting of an acrylonitrile-butadiene-styrene copolymer resin, a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane can be used. In the connection method of the present invention, any of the above resins can be used as a material of the synthetic resin member.

The connection method of the present invention can be suitably used for connection of members for which use of an adhesive itself or solvents contained in an adhesive is not suitable. For example, the connection method of the present invention can be particularly suitably used in the case where the above cylindrical body is a drip chamber made of a transparent soft resin selected from either a polypropylene or an olefinic elastomer and having a flange at an end at which the drip chamber is connected to the synthetic resin member, and the above synthetic resin member is a spike needle made of a synthetic resin selected from the group consisting of an acrylonitrile-butadiene-styrene copolymer resin, a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane and whose bucklingly deformed portion becomes whitened, having a lagging tube to be fitted onto the flange and having a contact portion to be in contact with the flange of the drip chamber at the base of the lagging tube. In a method of connecting the drip chamber and the spike needle with each other, the tip of the lagging tube is bucklingly deformed toward the cylindrical body by exerting only an external force on the tip of the lagging tube with the flange in contact with the contact portion, and the flange is held and locked between the bucklingly deformed tip of the lagging tube and the contact portion.

Further, the connection method of the present invention can also be applied to connection of a member to be connected which has a flange at an end at which a synthetic resin member is connected to the member with a bucklingly deformable synthetic resin member having an overhanging portion which overhangs the flange. In this case, the synthetic resin member is made of a synthetic resin which is selected from the group consisting of an acrylonitrile-butadiene-styrene copolymer resin, a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane and whose bucklingly deformed portion becomes whitened, the overhanging portion of the synthetic resin member is disposed outside the flange of the member to be connected, the tip of the overhanging portion is bucklingly deformed toward the member to be connected by exerting only an external force on the tip of the overhanging portion to such an extent that stress rupture does not occur, and the flange is locked by the bucklingly deformed tip of the overhanging portion.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is an illustrative, enlarged cross sectional diagram showing the essential portion of the members shown in FIG. 1, FIGS. 3(a) and 3(b) are illustrative cross sectional diagrams showing one embodiment of the connection method of the present invention, and FIG. 4 is a front view of another embodiment of the connection method of the present invention.

BEST MODES FOR CARRYING OUT THE INVENTION

An example of the present invention will be described in more detail with reference to the attached drawings hereinafter.

Figure 1:
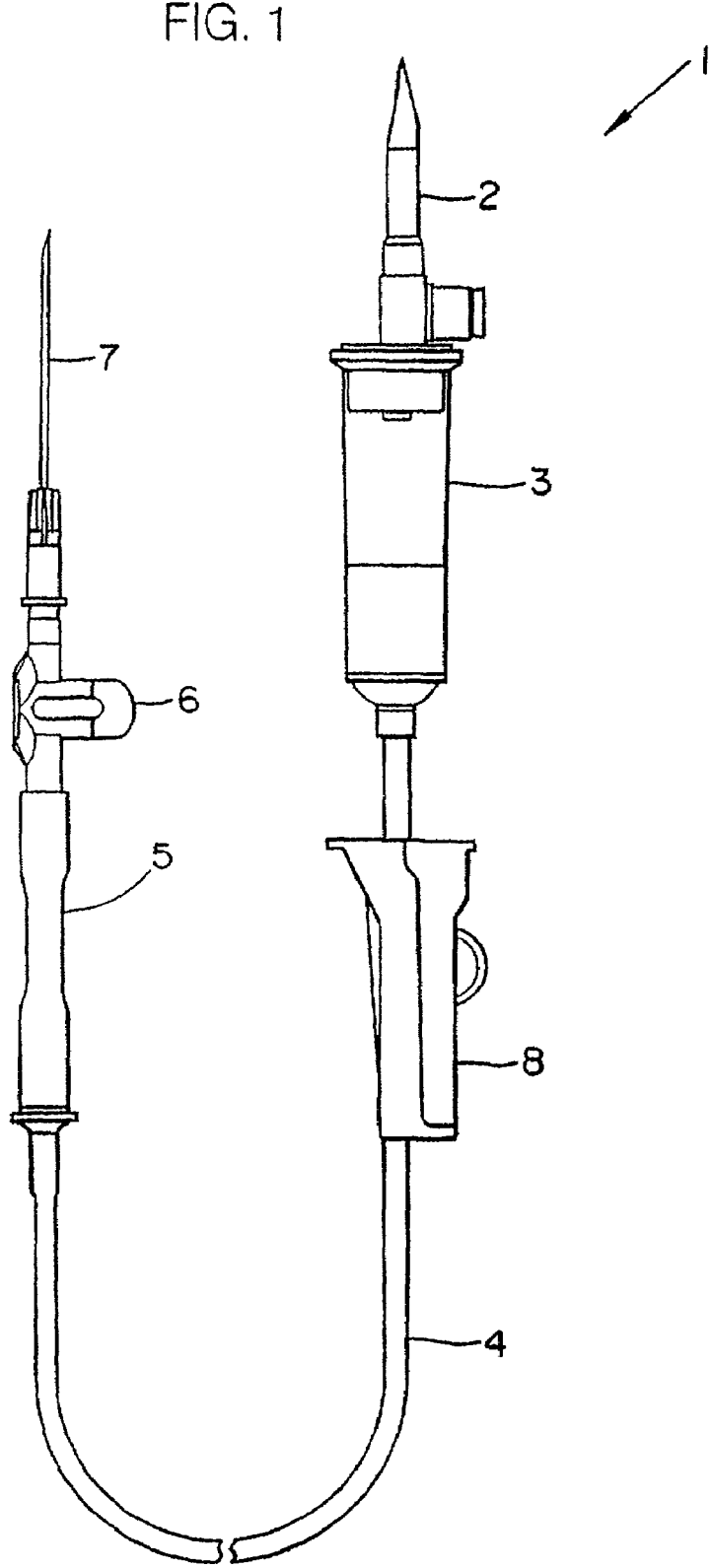
FIG. 1 is an illustrative diagram showing one exemplary constitution of members to which the connection method of the present invention is applied.

The connection method of the present invention is applied to a transfusion set 1 shown in FIG. 1.

The transfusion set 1 is used as a medical instrument for giving a liquid such as a drug to a living body. The transfusion set 1 comprises a spike needle 2 which pierces a liquid container such as a transfusion bag which is not shown and a drip chamber 3 which is connected to the lower end of the spike needle 2 and has a substantially cylindrical shape.

The transfusion set 1 further comprises a conduit tube 4 which is connected to the lower end of the drip chamber 3, and an intravenous injection needle 7 which pierces a living body is attached, via a multiple tube 6, to a rubber tube 5 which is connected to the conduit tube 4.

The spike needle 2 is formed of an acrylonitrile-butadiene-styrene copolymer resin (ABS resin) since it is required to have sufficient hardness to pierce a sealing rubber cap attached to the transfusion bag.

Meanwhile, the drip chamber 3 is formed of a transparent resin so that a dripping state of a liquid such as a drug which is provided from the liquid container can be observed. Further, the drip chamber 3, in cooperation with a clamp roller 8 which is attached in the middle of the conduit tube 4, makes fine adjustments to a dripping amount of the liquid such as a drug and pumps and introduces a drug or the like by being squeezed and released repeatedly at the start of transfusion.

Therefore, the drip chamber 3 is made of a transparent soft resin such as a polypropylene or an olefinic elastomer.

In the present example, the case where a drip chamber 3 which is made of a polypropylene is used as a cylindrical body and a spike needle 2 which is made of an ABS resin is used as a synthetic resin member to be connected to the cylindrical body will be described as an example.

As shown in FIG. 2, the spike needle 2 has a sharp tip 11 which pierces a sealing rubber cap (not shown) of a transfusion bag and an internal channel 12 which opens at the tip 11.

The channel 12 is a channel for leading a liquid such as a drug contained in the transfusion container to the drip chamber 3.

Further, a vent line 13 is also provided in parallel to the channel 12 in the spike needle 2 and opens at the tip 11 as in the case of the channel 12.

At the other end of the vent line 13, a bypass 14 is provided so as to allow the vent line 13 to communicate with outside air freely.

The bypass 14 is sealed by means of a cap 15 when there is no need to cause the vent line 13 to communicate with outside air.

From the rear end of the spike needle 2 is protruding a nozzle 16 which communicates with the base of the channel 12.

Around the nozzle 16, a cylindrical portion 17 which is to be fitted into the drip chamber 3 is formed.

In addition, around the cylindrical portion 17, a lagging tube 19 is formed with a space 18 therebetween.

The drip chamber 3 has a cylindrical body 20 and has a flange 22 formed on the outer edge of an opening 21 provided at an end at which the spike needle 2 is connected to the body 20.

The body 20 is formed such that it tapers down from the flange 22 toward the other end, and a connecting portion 24 having a valve 22 is formed at the end having a reduced diameter. To the connecting portion 24, the conduit tube 4 shown in FIG. 1 is connected.

Figure 3A:
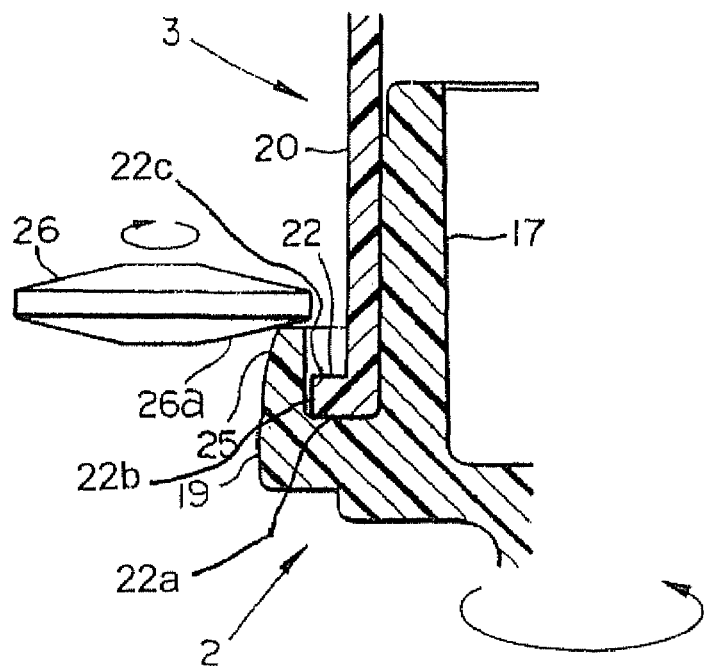

In the present example, firstly, as shown in FIG. 3(a), the flange 22 of the drip chamber 3 is pressed into the space 18 between the cylindrical portion 17 and lagging tube 19 of the spike needle 2 and brought into contact with the bottom of the space 18.

Then, the drip chamber 3 and the spike needle 2 are held and fixed together by means of a holding member that is not shown with the flange 22 in contact with the bottom of the space 18 as described above, and a roller 26 is pressed against a tip 25 of the lagging tube 19, thereby bucklingly deforming the tip 25. As a result, as shown in FIG. 3(b), the tip 25 is bucklingly deformed toward the body 20 of the drip chamber 3 and forms a locked potion 27, thereby locking the flange 22 of the drip chamber 3 and connecting the drip chamber 3 so as to prevent the drip chamber 3 from falling off in an axial direction.

Figure 3B:
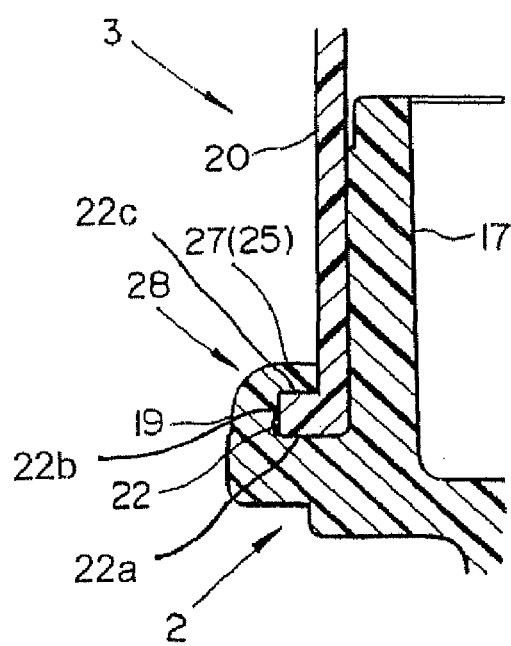

In FIG. 3(b), the roller 26 is pressed against the tip 25 by means of an air cylinder (not shown) or the like which is disposed in parallel to the axial direction of the drip chamber 3.

The roller 26 is pivoted coaxially by the air cylinder to be freely rotatable, and when the spike needle 2 is rotated around an axis, the roller 26 is pressed against the tip 25 while rotating together with the spike needle 2.

In addition, the roller 26 has a tapered portion 26a formed at the tip and is pressed against the tip 25 with the tapered portion 26a in contact with the tip 25.

As a result, stress can be applied to the tip of the lagging tube uniformly, and the tip of the lagging tube can be bucklingly deformed to the extent that stress rupture does not occur. Further, formation of friction scars on the tip 25 of the lagging tube 19 can be prevented.

In the present example, for example, with the roller 26 pressed against the lagging tube 19 having a thickness of 1 mm with a pressing force of 10 to 25 kgf, the spike needle 2 is rotated around an axis at a speed of 200 to 1,200 rpm. Thereby, the tip 25 of the lagging tube 19 can be bucklingly deformed about 1 second, and a bonding strength of about 30 kgf can be obtained.

When the revolution speed of the spike needle 2 is higher than 1,200 rpm, the tip 25 slips on a surface on which the tip 25 is in contact with the roller 26 due to a decrease in contact friction force, whereby poor appearance such as rough texture may be formed. On the other hand, when the revolution speed of the spike needle 2 is lower than 200 rpm, stress is not uniformly dispersed easily, whereby distortion may occur. Therefore, the revolution of the spike needle 2 is preferably set to be 400 to 600 rpm to ensure that the above inconveniences are prevented.

When the tip 25 is bucklingly deformed as described above, the bucklingly deformed, bended portion 28 becomes whitened.

Accordingly, in the present example, the whitening phenomenon is used not only as a measure of buckling deformation but also for evaluating the quality of a product.

That is, when the bended portion 28 is whitened, the portion has been bucklingly deformed, and there is no possibility that it restores its original state with time or by application of heat.

However, when the bended portion 28 is not whitened, there is a possibility that the portion may restore its original state, and a product can be determined to be defective from its appearance immediately.

According to the connection method of the present example, the flange 22 is pressed into the space 18 between the cylindrical portion 17 and lagging tube 19 of the spike needle 2, whereby the drip chamber 3 can secure fluid-tightness.

Further, since the flange 22 is held between the lagging tube 19 and the locked portion 27, there is no possibility that the drip chamber 3 may undergo fluid leakage or fall off during pumping.

In the above example, the roller 26 is pressed against the tip 25 of the lagging tube 19 to bucklingly deform the tip 25 so as to form the locked portion 27.

As illustrated in FIGS. 3(a) and 3(b), the flange 22 includes a first surface 22a, a second surface 22b and a third surface 22c at an end to be connected with the synthetic resin member. The tip 25 of the overhanging portion is bucklingly deformed toward the member to be connected so that the overhanging portion is in contact with the first surface 22a, the second surface 22b and the third surface 22c of the flange 22.

Alternatively, the tip 25 may be bucklingly deformed as shown in FIG. 4.

In a method shown in FIG. 4, with the flange 22 of the drip chamber 3 pressed into the space 18 between the cylindrical portion 17 and lagging tube 19 of the spike needle 2, the spike needle 2 is caused to pass between a pair of plate members 29a and 29b while rotated around an axis.

The space between the plate members 29a and 29b tapers down from an inlet 30 toward an outlet 31, and the tip 25 is bucklingly deformed when passing between the plate members 29a and 29b, thereby forming the locked portion 27 shown in FIG. 3(b).

The revolution speed of the spike needle 2 is set to be 200 to 1,200 rpm, preferably 400 to 600 rpm, as appropriate due to the same reason as that in the case shown in FIG. 3.

When the revolution speed of the spike needle 2 is within the above range, the tip 25 of the lagging tube 19 can be bucklingly deformed about 1 second.

The plate members 29a and 29b may be disposed linearly or in a curve so as to form portions of a circumference when viewed flat.

Further, the lengths of the plate members 29a and 29b and the speed of the spike needle 2 when passing between the plate members 29a and 29b are set such that the tip 25 of the lagging tube 19 can be bucklingly deformed about 1 second when the spike needle 2 is rotated at the revolution speed.

In the above examples, the case where the drip chamber 3 which is made of a polypropylene having poor adhesion to an ABS resin is connected to the spike needle 2 which is made of an ABS resin is described as an example.

However, the drip chamber 3 may be made of an olefinic elastomer having poor adhesion to an ABS resin just as in the case of a propylene or may be made of other resins such as a soft polyvinyl chloride which has good adhesion to an ABS resin.

Further, in the above examples, the case where the spike needle 2 and drip chamber 3 of the transfusion set 1 used as a medical instrument are connected to each other is described.

However, the connection method of the present invention can also be applied to the case where a cylindrical body of another medical instrument or member is connected to a synthetic resin member.

In this case, in the above examples, with the flange 22 of the drip chamber 3 (cylindrical body) in contact with the base (bottom of the space 18 between the cylindrical portion 17 and the lagging tube 19) of the lagging tube 19 of the spike needle 2 (synthetic resin member), the tip 25 of the lagging tube 19 is bucklingly deformed.

However, the synthetic resin member does not necessarily have the portion which makes contact with the flange of the cylindrical body as long as the cylindrical body and the synthetic resin member are fixed by means of a holding member or the like in such a position that the tip of the lagging tube can be bucklingly deformed so as to lock the flange of the cylindrical body.

In addition, the cylindrical body may be made of any material such as metal, glass or ceramic in addition to the synthetic resin such as a polypropylene, an olefinic elastomer or a soft polyvinyl chloride.

Meanwhile, in addition to the ABS resin, the synthetic resin member may be made of any synthetic resin which is bucklingly deformed to the extent that stress rupture does not occur when stress is applied.

However, since occurrence of buckling deformation can be easily determined based on emergence of whitening, a resin selected from the group consisting of a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane may be used as a material of the synthetic resin member in addition to the ABS resin.

INDUSTRIAL APPLICABILITY

The present invention can be used for connection of a synthetic resin member and other members such as a synthetic resin, metal, glass and ceramic regardless of the degree of adhesion between the members to be connected. The present invention can be particularly suitably used for connection of medical instruments or the like for which use of an adhesive itself or solvents contained in an adhesive is not suitable.

The invention claimed is:

1. A method for connecting a member comprising the following steps:
   providing a member to be connected, said member having a flange at an end to be connected with a synthetic resin member having an overhanging portion which overhangs the flange and is made of a bucklingly deformable synthetic resin;
   selecting the synthetic resin member to be made of a synthetic resin which is selected from the group consisting of an acrylonitrile-butadiene-styrene copolymer resin, a polystyrene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane and whose bucklingly deformed portion becomes whitened;
   disposing the overhanging portion of the synthetic resin member over the flange of the member to be connected, a tip of the overhanging portion being bucklingly deformed toward the member to be connected so that an inner circumferential surface of the tip of the overhanging portion is in contact all around the circumferential surface of an end of the flange and an end surface of the tip of the overhanging portion is in contact all around the external circumferential surface of the member to be connected by exerting only an external force on the tip of the overhanging portion to the extent that stress rupture does not occur; and locking the flange by the bucklingly deformed tip of the overhanging portion to provide a fluid tight seal and to prevent rotation therebetween.

2. The method according to claim 1, wherein the bucklingly deformation has a contact portion to be in contact with the flange of a member to be connected at the base of the overhanging portion, the tip of the overhanging portion is bucklingly deformed toward the member to be connected with the flange in contact with the contact portion, and the flange is held and locked between the bucklingly deformed tip of the overhanging portion and the contact portion.

3. The method according to claim 1, wherein the buckling deformation is carried out by pressing a rotatably pivoted roller, while rotating, against the tip of the overhanging portion continuously with a predetermined pressing force for a given time period.

4. The method according to claim 1, wherein a member to be connected is a cylindrical body having a flange at an end to be connected and the overhanging portion which overhangs the flange is a lagging tube to be fitted onto the flange.

5. A method according to claim 4, wherein the cylindrical body is a drip chamber made of a transparent soft resin selected from either a polypropylene or an olefinic elastomer and the synthetic resin member is a spike needle having a contact portion to be in contact with the flange of the drip chamber at the base of the lagging tube.

6. The method according to claim 1, wherein the flange has a first surface, a second surface and a third surface at an end to be connected with the synthetic resin member and the tip of the overhanging portion is bucklingly deformed toward the member to be connected so that the overhanging portion is in contact with the first surface, the second surface and the third surface of the flange.

7. A method for connecting a member comprising the following steps:

providing a member to be connected, said member having a flange at an end to be connected with a synthetic resin member having an overhanging portion which overhangs the flange and is made of a bucklingly deformable synthetic resin; selecting the synthetic resin member to be made of a synthetic resin which is selected from the group consisting of an acrylonitrile-butadiene-styrene copolymer resin, a polystryene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane and whose bucklingly deformed portion becomes whitened;

disposing the overhanging portion of the synthetic resin member over the flange of the member to be connected, a tip of the overhanging portion being bucklingly deformed toward the member to be connected so that an inner circumferential surface of the tip of the overhanging portion is in contact all around the circumferential surface of an end of the flange by exerting only an external force on the tip of the overhanging portion to the extent that stress rupture does not occur; and locking the flange by the bucklingly deformed tip of the overhanging portion to provide a fluid tight seal and to prevent rotation therebetween.

8. A method for connecting a member comprising the following steps:

providing a member to be connected, said member having a flange at an end to be connected with a synthetic resin member having an overhanging portion which overhangs the flange and is made of a bucklingly deformable synthetic resin; selecting the synthetic resin member to be made of a synthetic resin which is selected from the group consisting of an acrylonitrille-butadiene-styrene copolymer resin, a polystryene, a styrene copolymer, an acrylic resin, a polycarbonate, a polyvinyl chloride, a polymethyl methacrylate, a polyamide, a polyacetal, a polyethylene terephthalate, a fluorocarbon resin and a thermoplastic polyurethane and whose bucklingly deformed portion becomes whitened;

disposing the overhanging portion of the synthetic resin member over the flange of the member to be connected, a tip of the overhanging portion being bucklingly deformed toward the member to be connected so that an end surface of the tip of the overhanging portion is in contact all around the external circumferential surface of the member to be connected by exerting only an external force on the tip of the overhanging portion to the extent that stress rupture does not occur; and locking the flange by the bucklingly deformed tip of the overhanging portion to provide a fluid tight seal and to prevent rotation therebetween.

* * * * *